(12) United States Patent
Kaiser

(10) Patent No.: US 6,363,275 B1
(45) Date of Patent: Mar. 26, 2002

(54) DEVICE FOR DETECTING, FOR CHARACTERIZING BY DIFFERENTIAL DIAGNOSIS, AND TREATING TUMORS

(76) Inventor: Werner Alois Kaiser, Jagdweg 34, D-53757 Sankt Augustin (DE)

( * ) Notice: Subject to any disclaimer, the term of this patent is extended or adjusted under 35 U.S.C. 154(b) by 0 days.

(21) Appl. No.: 09/463,613
(22) PCT Filed: Jul. 23, 1998
(86) PCT No.: PCT/EP98/04615
§ 371 Date: Jan. 25, 2000
§ 102(e) Date: Jan. 25, 2000
(87) PCT Pub. No.: WO99/04689
PCT Pub. Date: Feb. 4, 1999

(30) Foreign Application Priority Data

Jul. 25, 1997 (DE) .......................................... 197 32 068
Jul. 25, 1997 (DE) .......................................... 197 32 067

(51) Int. Cl.[7] .................................................. A61B 5/05
(52) U.S. Cl. ...................................... 600/547; 600/372
(58) Field of Search ........................................ 600/547

(56) References Cited

FOREIGN PATENT DOCUMENTS

DE          4300018        3/1995
DE          4344986        7/1995
GB          2019579        10/1979
WO          WO9736192      10/1997
WO          WO9823204      6/1998

*Primary Examiner*—Robert L. Nasser
*Assistant Examiner*—Pamela Wingood
(74) *Attorney, Agent, or Firm*—Jordan and Hamburg LLP

(57) ABSTRACT

The invention relates to a device for detecting, using differential diagnosis, and for treating tumors. The inventive device enables, in practically one operation, a tumor-selective and tissue-protective representation, a reduction in the duration of treatment and/or an extension of the treatment to larger tissue areas. The device includes a combination of the following elements: at least one electrode pair (12, 13) having electrodes fitted substantially diametrically to the organism/organism part (10) in a cross-sectional plane; the electrode pair detecting resistance signals in different orientations in relation to the organism/organism part (10); a measuring device (17) for converting the resistance signals into resistance values; and an evaluation device (20) which receives the resistance values for evaluation and representation. The device has, furthermore, elements which ensure relative motion between the electrodes (12, 13) and the organism/organism part (10) at right angles to the cross-sectional plane; elements (22) which feed an electrolyte solution to the organism/organism part; and means (24) for treating the tissue of the organism/organism part (10).

8 Claims, 1 Drawing Sheet

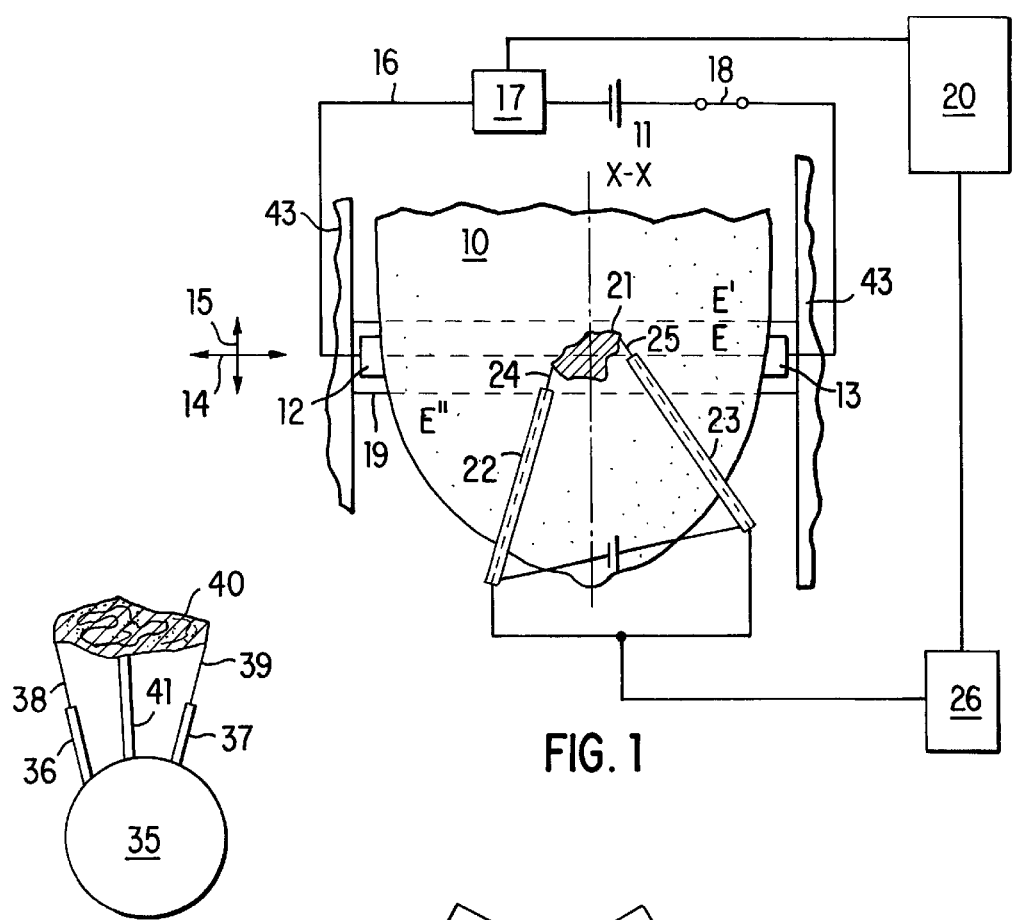
FIG. 1
FIG. 3
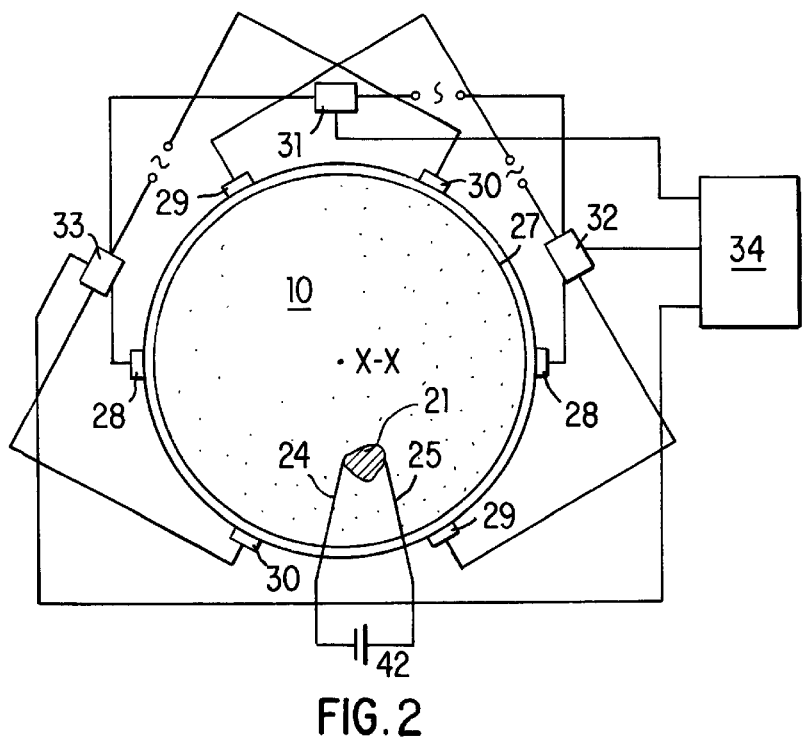
FIG. 2

DEVICE FOR DETECTING, FOR CHARACTERIZING BY DIFFERENTIAL DIAGNOSIS, AND TREATING TUMORS

BACKGROUND OF THE INVENTION

The invention relates to a device for detecting, for characterizing by differential diagnosis and for treating tumors according to the kind of the patent claims. Such a device is particularly suited for treating breast cancer.

A device for the non-invasive determination of the spatial distribution of electric impedances in the interior of a living being is known from the DE 42 43 628 A1. Furthermore, a method for the electric impedance imaging of animal living beings or human living beings by use of ionized metallic chelate is already known from the U.S. Pat. Specification No. 5,651,955 and the U.S. Pat. No. 5,733,525, wherein suitable contrast media are used and at least a part of a living being is imaged by exploiting impedances. In these references, there is not intended a right subsequent aftertreatment.

Furthermore, there is known the use of needles for the transurethral thermal ablation of hyperplasia of the prostate, refer to The Journal of Urology, vol. 156 (August 1996) pp. 413–419. However, this application is not connected with the generation of resistance images of an organism and an organ, respectively.

SUMMARY OF THE INVENTION

It is an object of the invention not only to achieve a tumor selective imaging which treats tissue with care, but also a reduction of the duration of treatment and/or an extension of the treatment to larger portions of tissue. That applies to both, the diagnosis and the therapy which directly follows the diagnosis, so the therapy is advantageously carried out at the same resistance image as the diagnosis is.

According to the invention the object is realized by the features of the claims. The generation and the evaluation of the impedance images of an organism or part of organism can be carried out either before or after adding the electrolyte solution or only after adding the electrolyte solution, however, prior to the therapeutical treatment procedure. In the latter case, a tumor typical threshold value should has to be defined prior. In particular, the enrichment of the electrolyte solution which preferably is a physiological saline solution favorably affects the diagnosis and the directly following treatment of the tumors. Thereby the resistance image of a tissue is made visible or in digital form and is intentionally inactivated by induction heating. Thereby the treatment can be carried out by a robot-like control of the needles

DETAILED DESCRIPTION OF THE INVENTION

The invention will be explained in more detail in the following by virtue of the schematic drawing illustrating three embodiments. There is shown in:

FIG. 1 a direct current operated inventional arrangement,

FIG. 2 a sectional view of an alternating current operated inventional arrangement, and FIG. 3 a front view of a catheter.

In FIG. 1, 10 designates a female breast, to which two preferably diametrally arranged electrodes 12, 13 are applied that are connected to a d. c. voltage source 11. The electrodes are adapted to be linearly displaced relative to the breast 10 together with or upon their carrier 19 in directions indicated by the double arrows 14, 15 and are rotatable about an axis X—X arranged in the drawing plane. The carrier 19, in turn, is displaceable along guides 43 parallel to the axis X—X. In the direct-current circuit 16 there are arranged a measuring instrument 17 and an on-off switch 18. The measuring instrument 17 is connected to an evaluation unit in which the measuring data derived from the measuring instrument 17 are evaluated and the resistance images are generated. The electrodes 12, 13 are adapted to be attached to the surface of the breast 10 by a counter-motion of the electrodes 12, 13, relative to and with, respectively, the carrier 19 in the direction of the double arrow 14. By rotating the carrier 19 about the axis X—X it is feasible to rotate the electrodes 12, 13 in any desired steps in a plane E which is at right angles to the drawing plane and, in these steps, to obtain the measuring data from the resistance in this disk of the breast 10. From these measuring data, the resistance image of the plane E is generated and made visible in file evaluation unit 20 through Fourier transformation and mathematical convolution (E. Kerstel, Bildgebende System für die medizinsche Diagnostik, $2^{nd}$ edition 1988, Siemens AG, Berlin/Munich, pp. 95–137). By said resistance image it is feasible to make visible the two-dimensional resistance distribution in said disk. Highly conductive object ranges are indicative of high resistance values, poorly conductive object ranges are indicative of high resistance values. In the same manner, voltage values can also be derived.

By displacement of the electrodes 12, 13 with the carrier 19 or upon the carrier 19 parallel to the axis X—X, resistance images of further planes (disks) E', E" are produced in analogy to the image generation in the computerized tomography by the absorption of X-rays, and are computed in the computer of the evaluation unit 20. In the presence of at least one tumor 21, the resistance images depart from one another or from a reference image not shown here, and make that the position and size of the tumor can be distinctly identified. In order to permit also the detection of small tumors, the planes E, E', E" etc. have to lie sufficiently near to one another.

Needles 24, 25 contained in protective envelopes 22, 23 are introduced into the organism part 10 for combating the tumor 21. Said needles heat up the tissue which is located between them by the aid of radio frequencies for a preselected period or in dependence of a real-time generated image of the tumor 21 which can be observed on a monitor of the evaluation unit 20. This actual image makes it possible to monitor the insertion of the needles 24, 25 and the inactivation of the tumor 21 in the course of treating the same.

The needles 24, 25 which are connected to a respective energy source (for example, current or radio frequency) can be maneuvered either manually or by an automatic and robot-like control 26 by virtue of the resistance images supplied by the evaluation unit 20. Thereby also very small tumors are precisely treatable.

When an electrolyte solution, for example, a physiological saline solution is injected intra-arterially, intravenously, for example, by the arm, or directly into the organism or into the organism part 10, then said solution is initially intensively enriched in the tumor 21, due to the tumor angiogenesis. By means of the above described arrangement, the resistance change, which an electrical current flow is opposed by the organism part 10, can be determined from the resistance image of the evaluation unit 20 with the aid of the resistance measurement, that is, from the data supplied by the measuring instrument 17, parallel to the enrichment of the electrolyte solution. Due to the intensified enrichment of the electrolyte solution in the first minutes after the injection, it is feasible to give a relatively clear judgement of a focal finding as being malignant or benigne. This is in analogy to the data from the image formation (refer to W. A. Kaiser, E. Zeitler: MR-imaging of the Breast: Fast Imaging Sequences with and without Gd-DTPA. Radiology 170 (1989), pp. 681–686).

If desired, a subtraction of the resistances or of the resistance images with and without electrolyte injection can intensify the effect of the tumor representation and localization in the evaluation unit 20. In the case of strongly vascularized tumors, a pure post-contrast image without a preceding native measurement can already yield a resistance below a threshold value which is typical of a tumor. In order to combat the localized tumor 21, the two (or a plurality of) needles 24, 25 which have been inserted into the tissue from the outside, engage the tumor or are positioned right adjacent to the tumor. Then the tumor 21 is inactivated by applying a current and/or a radio frequency, originating from a not shown source, preferably by the change of the membrane potentials or hyperthermia effects. This inactivation is enhanced and/or accelerated by a further administration of an electrolyte solution, for example, by a direct injection through a cannula. Thereby, the electrolyte injection is in particular adapted to render the thermal effect from the applied current and/or radio frequency, more homogeneous and more predeterminable.

In FIG. 2, an organism part 10 is enclosed by a rigid and electrically insulating shell 27 to maintain a constant shape during measurement and treatment. Said shell can be of basket design, in order to permit through wall apertures the passage of the needles 24, 25 for treatment, which are connected to a direct current source 42. In a regularly spaced arrangement three (or preferably a plurality of) pairs of electrodes 28, 29, 30 are displaceably positioned around the shell 27 in a cross-sectional plane E, parallel to an axis X—X, whereby said electrode pairs are operated with alternating current. Each of the pairs of electrodes is connected to an evaluation unit 34 via a resistance measuring instrument 31, 32, 33, which measures the resistance values in the tissue of the organism part 10 and feeds the same into the evaluation unit 34 for storage, generation of the resistance images and for the visualising and processing of the latter. The therapeutic treatment of a carcinoma 21 found in the course of the resistance measurement is part of this processing. As to the rest, the same is valid as disclosed in connection with FIG. 1.

In FIG. 3, there is shown a catheter 35 with two needles 38, 39 contained in protective envelopes 36, 37, said needles are extendible into and retractable from out the catheter 35 and are adapted to be applied to a carcinoma 40 under radio frequencies. At least one cannula 41 also extendible into and retractable from out the catheter 35 is adapted, manually or robot-controlled, for injecting a suitable liquid, for example, a physiological saline solution, prior to the application of radio frequencies for heating the organism tissue included between the needle points. As a result, the heating effect is increased and homogenized and, hence, the time for treatment of a patient is reduced and/or the treatment is extended to larger ranges of tissue. As to the rest, it is valid in analogy to the disclosure in connection with FIG. 1.

All features disclosed in the specification, in the subsequent claims, and represented in the drawings can be substantial for the invention individually, but also in any combination with one another.

LIST OF REFERENCE NUMERALS

10 breast
11, 42 d. c. voltage source
12, 13 electrodes
14, 15 double arrows
16 direct-current circuit
17 measuring instrument
18 switch
19 carrier
20, 34 evaluating unit
21 tumor
22, 23, 36, 37 protective envelopes
24, 25, 38, 39 needles
26 control
27 shell
28, 29, 30 pairs of electrodes
31, 32, 33 resistance measuring instruments
35 catheter
40 carcinoma
41 cannula
X—X axis
E, E', E" (sectional) plane

What is claimed is:

1. An arrangement for one of detecting and treating tumors in an organism using electrical resistance images comprising:
   at least one pair of electrodes arranged to receive the organism there between and aligned with a cross sectional plane of the organism, said at least one pair of electrodes being for deriving resistance signals from different orientations relative to the organism;
   a measuring instrument for converting said resistance signals into resistance values;
   an evaluation unit, said resistance values being fed into said evaluation unit for evaluation and imaging; and
   means for providing relative movement between the electrodes and the organism.

2. The arrangement as claimed in claim 1, further comprising means for affecting a tissue of said organism by one of hyperthermia and change of membrane potentials.

3. The arrangement as claimed in claim 2, further comprising: a means for supplying an electrolyte solution, and a catheter, wherein said means for supplying an electrolyte solution are cannulas and said means for affecting a tissue of the organism are needles which are arranged on the catheter and are extendible into and retractable from said catheter.

4. The arrangement as claimed in claim 3, further comprising a robot control provided for at least one of said needles and said cannulas.

5. The arrangement as claimed in claim 1, wherein the at least one pair of electrodes is arranged for rotation about an axis X—X.

6. The arrangement as claimed in claim 5, further comprising means for affecting a tissue of said organism by one of hyperthermia and change of membrane potentials.

7. The arrangement as claimed in claim 6, further comprising: a means for supplying an electrolyte solution; and a catheter, wherein said means for supplying an electrolyte solution are cannulas and said means for affecting a tissue of the organism are needles which are arranged on the catheter and are extendible into and retractable from said catheter.

8. The arrangement as claimed in claim 7, further comprising a robot control provided for at least one of said needles and said cannulas.

* * * * *